United States Patent [19]

Löher et al.

[11] Patent Number: 5,332,715
[45] Date of Patent: Jul. 26, 1994

[54] PLANT-PROTECTING SUBSTITUTED ISOXAZOLINES, ISOXAZOLES, ISOTHIAZOLINES AND ISOTHIAZOLES, AND ALSO PROCESSES FOR THEIR PREPARATION AND THEIR USE

[75] Inventors: Heinz-Josef Löher, Liederbach; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 952,895

[22] PCT Filed: May 29, 1991

[86] PCT No.: PCT/EP91/00989
§ 371 Date: Nov. 18, 1992
§ 102(e) Date: Nov. 18, 1992

[87] PCT Pub. No.: WO91/18907
PCT Pub. Date: Dec. 12, 1991

[30] Foreign Application Priority Data

Jun. 1, 1990 [DE] Fed. Rep. of Germany ....... 4017665

[51] Int. Cl.$^5$ .............. C07D 231/06; C07D 231/12; C07F 7/02
[52] U.S. Cl. ................................. 504/193; 544/69; 546/14; 548/110
[58] Field of Search ................. 548/110; 504/193; 546/14; 544/69

[56] References Cited

U.S. PATENT DOCUMENTS 3,274,210 9/1966 Frisch et al. ............... 260/307

FOREIGN PATENT DOCUMENTS 0249015 12/1987 European Pat. Off. ........... 546/14

OTHER PUBLICATIONS

CA 98(7):53987g Trimethylsilane Carbonitrile Oxide. Brandi et al., p. 683, 1983.

CA 99(3):22543a Synthesis . . . Oxide. De Sarlo et al., p. 628, 1983.
Synthesis, Trimethylsilane Carbonitrile Oxide, Brandi et al., pp. 719–721, 1982.
Heterocycles, vol. 20, No. 3, 1983, Synthesis . . . Oxide, DeSarlo et al., pp. 511–518.

*Primary Examiner*—Mary C. Lee
*Assistant Examiner*—Joseph K. McKane
*Attorney, Agent, or Firm*—Curtis, Morris & Safford

[57] ABSTRACT

Plant-protecting substituted isoxazolines, isoxazoles, isothiazolines and isothiazoles, and also processes for their preparation and their use
Compounds of the formula I $$(R^1)(R^2)(R^3)Si-A-Het-B-CO-Z \qquad (I)$$

where
Het is an isoxazole-, isoxazoline-, isothiazole- or isothiazoline-3,5-diyl radical,
A and B are a bond or alkylene,
$R^1$, $R^2$ and $R^3$ are substituted or unsubstituted, saturated or unsaturated alkyl or, if desired, phenylalkyl or phenyl,
Z is OH, OR where R is saturated or unsaturated, substituted or unsubstituted alkyl or substituted or unsubstituted phenyl or benzyl or trialkylsilylmethoxy, substituted or unsubstituted phenylamino or oxazolinyl or amino, mono- or dialkylamino or -hydrazino, cycloalkylamino, $NH_2NH_2$, pyridino, morpholino, dimethylmorpholino, a radical $-ON=CR^4R^5$ or $O-CHR^7-CO-OR^6$ where $R^4$, $R^5$=alkyl and/or $R^4CR^5$ is cycloalkyl and $R^6$, $R^7$ are H or a saturated or unsaturated acyclic hydrocarbon radical,
are suitable for protecting crop plants against phytotoxic side effects of herbicides.

14 Claims, No Drawings

PLANT-PROTECTING SUBSTITUTED ISOXAZOLINES, ISOXAZOLES, ISOTHIAZOLINES AND ISOTHIAZOLES, AND ALSO PROCESSES FOR THEIR PREPARATION AND THEIR USE

DESCRIPTION

The invention relates to safeners or antidotes which, in combination with herbicides, can reduce the phytotoxicity of the herbicides to crop plants.

The invention relates to plant-protecting compounds of the general formula (I) or salts thereof

in which

Het is a divalent heterocyclic radical from the group comprising the isothiazolines, isothiazoles or isoxazoles, and isoxazolines of the formulae (Ia) to (Id),

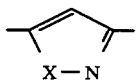

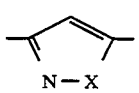

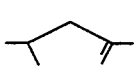

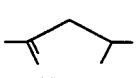

in which

X is an oxygen or sulfur atom,

A and B independently of one another in each case are a single bond or $C_1$-$C_4$-alkylene which is unsubstituted or monosubstituted or polysubstituted by $C_1$-$C_4$-alkyl, $R^1$, $R^2$ and $R^3$ independently of one another are alkyl, alkenyl, alkynyl or cycloalkyl, it being possible for the four last-mentioned radicals to be unsubstituted or mono- or polysubstituted by radicals from the group comprising alkoxy, alkylthio, mono- or dialkylamino, alkoxycarbonyl, alkylcarbonyloxy, cyano and halogen, furthermore phenylalkyl or phenyl which in each case are unsubstituted or mono- or polysubstituted in the phenyl radical by radicals from the group comprising alkyl, alkoxy, alkylthio, mono- and dialkylamino, alkoxycarbonyl, cyano and halogen, Z is hydroxyl or alkoxy, alkenyloxy, alkynyloxy, alkylthio, cycloalkoxy, phenoxy or benzyloxy, the 7 last-mentioned radicals being unsubstituted or mono- or polysubstituted by radicals from the group comprising alkoxy, alkylthio, mono- and dialkylamino, phenyl, substituted phenyl, cyano, haloalkyl, haloalkoxy and halogen, furthermore trialkylsilylmethoxy, a radical of the formula (Ie) or (If)

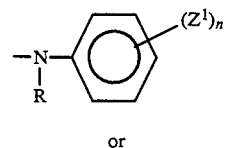

where R is hydrogen or alkyl, $Z^1$ radicals independently of one another are halogen, halogenoalkyl, halogenoalkoxy, alkyl, alkoxy or alkylthio and n is an integer from 0 to 5, or Z is furthermore amino, mono- or dialkylamino, cycloalkylamino, hydrazino, alkyl- or dialkylhydrazino, pyridino, morpholino, dimethylmorpholino, a radical of the formula (Ig),

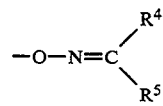

where $R^4$ and $R^5$ independently of one another are alkyl radicals or $R^4$ and $R^5$ together with the carbon atom linking them form a cycloalkyl radical, furthermore a radical of the formula (Ih),

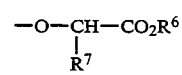

where $R^6$ and $R^7$ independently of one another are hydrogen or a saturated or unsaturated acyclic hydrocarbon radical.

In formula (I), alkyl, alkoxy, haloalkyl, haloalkoxy, alkylamino and alkylthio radicals in the alkyl moiety as well as the corresponding unsaturated and/or substituted radicals in the hydrocarbon moiety can in each case be straight-chain or branched. Alkyl radicals, also in the compound meanings such as alkoxy, haloalkyl etc., are, for example, methyl, ethyl, n- and i-propyl, n-, i-, t- and 2-butyl, the isomeric pentyl, hexyl, heptyl, octyl, nonyl, decyl, undecyl and dodecyl radicals, and also the longer-chain fatty alkyl radicals having up to 24 carbon atoms. Alkenyl and alkynyl radicals mean the unsaturated radicals which are possible and which correspond to the alkyl radicals, preferably ($C_2$-$C_{12}$)-alkenyl and -alkynyl radicals. Halogen is fluorine, chlorine, bromine or iodine, preferably fluorine, chlorine or bromine, in particular fluorine or chlorine.

In the case where Z=OH, the compounds of the formula (I) can form salts. Salts which can be employed according to the invention are those which can be used in agriculture. Examples of suitable salts are metal salts such as alkali metal salts or alkaline earth metal salts, in particular sodium salts or potassium salts, ammonium salts or substituted ammonium salts which are mono- to tetrasubstituted by alkyl and/or alkanol radicals having preferably up to 4 carbon atoms.

Formula (I) furthermore also embraces all stereoisomers and their mixtures, in particular also pure enantiomers and their mixtures (for example racemates). Stereoisomers can occur mainly when asymmetric carbon atoms or suitably substituted double bonds are present in the formula (I). An example of an asymmetric carbon atom is the carbon atom bonded to the oxygen atom in the isoxazoline ring.

Plant-protecting compounds of the formula (I) according to the invention, or salts thereof, which are of particular interest are those in which Z is hydroxyl, $C_1$–$C_6$-alkoxy, $C_2$–$C_6$-alkynyloxy, $C_2$–$C_6$-alkynyloxy, $C_1$–$C_6$-alkylthio, $C_3$–$C_6$-cycloalkoxy, phenoxy or benzyloxy, the 7 last-mentioned radicals being unsubstituted or mono- or polysubstituted by radicals from the group comprising $C_1$–$C_4$-alkoxy, mono- or di-($C_1$–$C_4$-alkyl)amino, $C_1$–$C_4$-alkylthio, $C_1$–$C_4$-haloalkyl, $C_1$–$C_4$-haloalkoxy, cyano and halogen, or Z is furthermore tri($C_1$–$C_4$-alkyl)silylmethoxy, furthermore a radical of the formula (Ie) or (If) mentioned, in which R in each case is hydrogen or ($C_1$–$C_4$)-alkyl, $Z^1$ is halogen and n is 0, 1, 2, 3, 4 or 5, or Z is furthermore amino, mono- or di-($C_1$–$C_4$-alkyl)amino, $C_5$–$C_6$-cycloalkylamino, hydrazino, piperidino, morpholino or 2,6-dimethylmorpholino, a radical of the formula (Ig) mentioned where $R^4$ and $R^5$ independently of one another are $C_1$–$C_4$-alkyl or $R^1$ and $R^2$ together with the carbon atom linking them form a 5-, 6- or 7-membered cycloalkyl radical, or Z is a radical of the formula (Ih) mentioned where $R^6$ and $R^7$ independently of one another are hydrogen or $C_1$–$C_6$-alkyl, $C_2$–$C_6$-alkyl or $C_2$–$C_6$-alkynyl.

Compounds of the formula (I) according to the invention, or salts thereof, which are of particular interest are those where $R^1$, $R^2$ and $R^3$ independently of one another are $C_1$–$C_{18}$-alkyl, $C_2$–$C_{18}$-alkenyl, $C_2$–$C_{18}$-alkynyl or $C_3$–$C_{18}$-cycloalkyl, the 4 last-mentioned radicals being unsubstituted or mono- or polysubstituted by radicals from the group comprising $C_1$–$C_4$-alkyl, $C_1$–$C_4$-alkylthio, mono- or di-($C_1$–$C_4$-alkyl)amino, ($C_1$–$C_4$-alkoxy)carbonyl, ($C_1$–$C_4$-alkyl)carbonyloxy, cyano and halogen, furthermore phenyl-($C_1$–$C_4$-alkyl) or phenyl, the 2 last-mentioned radicals being unsubstituted or mono- or polysubstituted by radicals from the group comprising $C_1$–$C_4$-alkyl, $C_1$–$C_4$-alkoxy, $C_1$–$C_4$-alkylthio, mono- and di-($C_1$–$C_4$-alkyl)amino, cyano and halogen.

Preferred compounds of the formula (I) according to the invention, or salts thereof, are those where Z is hydroxyl, $C_1$–$C_4$-alkoxy, $C_2$–$C_4$-alkenyloxy, $C_2$–$C_4$-alkynyloxy, $C_1$–$C_4$-alkylthio, phenoxy or benzyloxy, the 6 last-mentioned radicals being unsubstituted or mono- or polysubstituted by radicals from the group comprising $C_1$–$C_4$-alkyl, $C_1$–$C_4$-alkoxy, $C_1$–$C_4$-alkylthio, mono- or di-($C_1$–$C_4$-alkyl)amino, cyano and halogen, furthermore tri-($C_1$–$C_2$-alkyl)-silylmethoxy, a radical of the formula (Ie) or (If) mentioned where R is hydrogen or $C_1$–$C_4$-alkyl, $Z^1$ is halogen and n is 0–5, furthermore mono- and di-($C_1$–$C_4$-alkyl)amino, $C_5$–$C_6$-cycloalkylamino, a radical of the formula (Ih) mentioned where $R^6$ is $C_1$–$C_4$-alkyl, $C_2$–$C_4$-alkenyl or $C_2$–$C_6$-alkynyl and $R^7$ is hydrogen or methyl.

Other preferred compounds of the formula (I) according to the invention, and salts thereof, are those where A is a direct bond or $C_1$–$C_2$-alkylene, preferably a direct bond or $CH_2$, and B is a direct bond or $C_1$–$C_2$-alkylene, preferably a direct bond or $CH_2$.

Equally, preferred compounds of the formula (I) according to the invention, or salts thereof, are those where $R^1$, $R^2$ and $R^3$ independently of one another are $C_1$–$C_6$-alkyl, in particular methyl, ethyl, n- or i-propyl, n-, i-, t- or 2-butyl, pentyl, n-, i- and 2-hexyl, phenyl or benzyl. Particularly preferred compounds of the formula (I) according to the invention are those in which A, B, Z, $Z^1$, n, R, $R^1$, $R^2$, $R^3$ and X in each case have meanings which have been mentioned as being preferred.

The present invention also relates to a process for the preparation of the compounds of the formula (I) and salts thereof, which comprises reacting a compound of the formula (II) or (III)

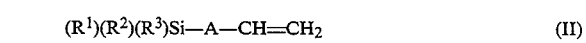  (II)

  (III)

where $R^1$, $R^2$, $R^3$ and A have the meanings given in the case of formula (I), with a nitrile oxide of the formula (IV),

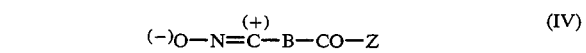  (IV)

where Z and B have the meanings given in the case of formula (I), or reacting a compound of the formula (V) or (VI),

  (V)

  (VI)

where B and Z have the meanings given in the case of formula (I), with a compound of the formula (VII)

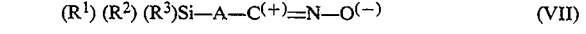  (VII)

where $R^1$, $R^2$, $R^3$ and A have the meanings mentioned above in the case of formula (I).

Suitable solvents for the reactions are nonpolar organic solvents, for example ethers such as diethyl ether or THF. However, the reactions can also be carried out in the absence of solvents.

The starting compounds of the formulae (II) and (VII) are known from the literature (cf. *J. Org. Chem.* 25, 1160 (1960); *J. Med. Chem.* 17 (1974), 549–552; *J. Chem. Soc. Chem. Commun.* 1984, 968–969; *Can. J. Chem.* 41, 2980 (1963), *J. Am. Chem. Soc.* 95, 6152 (1973), Fieser and Fieser in *Reagents for Organic Synthesis* 10, 6 and 11, 16; and the particular references mentioned therein) or can be prepared analogously to the compounds which are known.

The compounds of the formula (I) reduce or inhibit phytotoxic side effects which can occur when herbicides are employed in crops of useful plants.

The compounds of the formula (I) and the herbicidal active substances can be applied together or one after the other, in any sequence desired. The compounds of the formula (I) are then capable of reducing, or completely compensating for, harmful side effects of the herbicides in crop plants, without impairing the activity of these herbicides against harmful plants.

As a result of this, the field of application of conventional plant protection agents can be widened very considerably. Such compounds which possess the property of protecting crop plants against phytotoxic damage by herbicides are called "antidotes" or "safeners".

Examples of herbicides whose phytotoxic side effects can be reduced by means of the compounds of the formula (I) are carbamates, thiocarbamates, haloacetanilides, substituted phenoxy-, naphthoxy-, phenoxyphenoxy-, benzyloxyphenoxy- and heteroaryloxyphenoxy-carboxylic acid derivatives as well as cyclohexanedione derivatives. Examples of heteroaryloxyphenoxy-carboxylic acid derivatives are quinolyloxy-, quinoxalyloxy-, pyridyloxy-, benzoxazolyloxy- and benzothiazolyloxy-phenoxycarboxylic acid esters. Preferred compounds are phenoxyphenoxy- and heteroaryloxyphenoxy-carboxylic acid esters. Suitable esters in this connection are, in particular, lower alkyl, alkenyl and alkynyl esters.

The following herbicides may be mentioned by way of example but without imposing any restriction:

A) Herbicides of the type of the ($C_1$–$C_4$) alkyl, ($C_2$–$C_4$)-alkenyl or ($C_3$–$C_4$)alkynyl phenoxyphenoxy-, benzylphenoxy and heteroaryloxyphenoxy-carboxylates, such as methyl 2-(4-(2,4-dichlorophenoxy)-phenoxy)propionate, methyl 2-(4-(4-bromo-2-chlorophenoxy)phenoxy)propionate, methyl 2-(4-(4-trifluoromethylphenoxy)phenoxy)propionate, methyl 2-(4-(2-chloro-4-trifluoromethylphenoxy)phenoxy)propionate, methyl 2-(4-(2,4-dichlorobenzyl)phenoxy)propionate, ethyl 4-(4-(4-trifluoromethylphenoxy)phenoxy)pent-2-enoate, ethyl 2-(4-(3,5-dichloropyridyl-2-oxy)-phenoxy)propionate, propargyl 2-(4-(3,5-dichloropyridyl-2-oxy) phenoxy)propionate, ethyl 2-(4-(6-chlorobenzoxazol-2-yloxy)phenoxy)propionate, methyl 2-(4-(3-chloro-5-trifluoromethyl-2-pyridyloxy)phenoxy)propionate, butyl 2-(4-(5-trifluoromethyl-2-pyridyloxy)phenoxy)propionate, methyl 2-(4-(3-fluoro-5-chloropyridyl-2-oxy) phenoxy)propionate, propargyl 2-(4-(3-fluoro-5-chloropyridyl-2-oxy)phenoxy)propionate, methyl 2-(4-(6-chloro-2-quinoxalyloxy)phenoxy)-propionate, methyl 2-(4-(6-fluoro-2-quinoxalyloxy)-phenoxy)propionate, methyl 2-(4-(6-chloro-2-quinolyloxy)phenoxy)propionate, 5-methoxycarbonylmethyl 2-(4-(5-chloro-3-fluoropyridin-2-yloxy)phenoxy)thiopropionate, B) Chloroacetanilide herbicides, such as N-methoxymethyl-2,6-diethylchloroacetanilide, N-(3'-methoxyprop-2'-yl)methyl-6-ethylchloroacetanilide, N-(3-methyl-1,2,4-oxadiazol-5-ylmethyl)-2,6-dimethylchloroacetanilide, C) Thiocarbamates, such as S-ethyl N,N-dipropylthiocarbamate or S-ethyl N,N-diisobutylthiocarbamate, D) Cyclohexanedione derivatives, such as methyl 3-(1-allyloxyimino)butyl-4-hydroxy-6,6-dimethyl-2-oxocyclohex-3-enecarboxylate 2-(N-ethoxybutyrimidoyl)-5-(2-ethylthiopropyl)-3-hydroxy-2-cyclohexen-1-one, 2-(N-ethoxybutyrimidoyl)-5-(2-phenylthiopropyl)-3-hydroxy-2-cyclohexen-1-one, 2-(1-allyloxyiminobutyl)-4-methoxycarbonyl-5,5-dimethyl-3-oxocyclohexenol, 2-(1-(3-chloroallyloxy)iminobutyl)-5-(2-ethylthio)propyl)-3-hydroxycyclohex-2-enone 2-[1-(ethoxyimino)butyl]-3-hydroxy-5-(thian-3-yl)cyclohex-2-enone or 2-(1-ethoxyiminopropyl)-5-(2,4,6-trimethylphenyl)-3-hydroxy-2-cyclohexen-1-one.

The ratio of safener:herbicide can vary within wide limits, preferably in the range between 1:10 and 10:1, in particular between 2:1 and 1:10. The amounts of herbicide and safenet which are ideal in each case depend on the type of the herbicide used or on the safener used as well as on the nature of the plant stand to be treated, and they can be determined for each individual case by appropriate experiments.

The safeners are mainly employed in particular in cereal crops (wheat, rye, barley, oats), rice, maize and sorghum, but also in cotton, sugar beet, sugar cane and soya bean.

Depending on their properties, the safeners of the formula (I) can be used for pre-treating the seed of the crop plant (seed dressing), or they can be incorporated in the seed furrows prior to sowing, or used together with the herbicide prior to, or after, plant emergence.

Pre-emergence treatment includes both the treatment of the area under cultivation prior to sowing and treatment of the areas under cultivation where seed has been sown but growth of the crop plants has not yet taken place. The application together with the herbicide is preferred. Tank mixes or ready mixes can be employed for this purpose.

The required application rates of the compounds of the formula (I) can vary within wide limits, depending on the indication and the herbicide used, and they generally vary between 0.01 and 10 kg of active substance per hectare.

The present invention thus also relates to a method of protecting crop plants from phytotoxic side effects of herbicides, which comprises applying an effective amount of a compound of the formula (I) before, after or simultaneously with the herbicide to the plants, seeds of plants, or the area under cultivation.

Moreover, the compounds according to the invention exhibit growth-regulatory properties in crop plants. They engage in the plant metabolism in a regulating fashion and can therefore be employed for facilitating harvests such as, for example, by triggering desiccation, abscission and stunted growth. Furthermore, they are also suitable for generally controlling and inhibiting undesirable vegetative growth, without killing the plants in the process. Inhibition of vegetative growth is very important in many monocotyledon and dicotyledon cultures since lodging can be reduced, or completely inhibited, by this process.

The compounds of the formula I or their combinations with one or more of the herbicides or groups of herbicides mentioned can be formulated in a variety of ways, as predetermined by the biological and/or chemiophysical parameters. The following possibilities are therefore suitable for formulation: wettable powders (WP), emulsifiable concentrates (EC), water-soluble powders (SP), water-soluble concentrates (SL), concentrated emulsions (EW) such as oil-in-water and water-in-oil emulsions, sprayable solutions or emulsions, capsule suspensions (CS), dispersions on an oil or water basis (SC), suspoemulsions, suspension concentrates (SC), dusting agents (DP), solutions which are miscible with oil (OL), seed-dressing agents, granules (GR) in the form of microgranules, spray granules, coated granules and adsorption granules, soil granules or granules for broadcasting (FG), water-soluble granules (SG), water-dispersible granules (WG), ULV formulations, microcapsules and waxes.

These individual formulation types are known in principle and are described, for example, in: Winnacker-Küchler, "Chemische Technologie [Chemical Technology]", Volume 7, C. Hauser Verlag Munich, 4th Ed., 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a readymix or as a tank mix.

The invention therefore relates to the agents which contain the compounds of the formula (I) according to the invention. These are mainly, on the one hand, plant-protecting agents which contain one or more compounds of the formula (I) and customary inert auxiliaries which correspond to the particular type of formulation, and, on the other hand, herbicidal agents which contain a combination of compounds of the formula (I) and one or more herbicides and the customary auxiliaries which correspond to the particular type of formulation.

Wettable powders are preparations which are uniformly dispersible in water and which, besides the active substance, also contain wetting agents, for example polyoxyethylated alkylphenols, polyoxyethylated fatty alcohols and fatty a mines, alkanesulfonates or alkylarylsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance. Emulsifiable concentrates are prepared by dissolving the active substance in an organic solvent, for example butanol, cyclohexanone, dimethylformamide, xylene and also higherboiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block copolymers), alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite or diatomaceous earth.

Soil granules or granules for broadcasting can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 0.1 to 95% by weight, of active substance of the formula (I), or of active substance mixture antidote/herbicide, 1 to 99% by weight, in particular 5 to 99.8% by weight, of a solid or liquid additive and 0 to 25% by weight, in particular 0.1 to 25% by weight, of a surfactant.

The concentration of active substance in wettable powders is, for example, about 10 to 90% by weight, the remainder to 100% by weight is composed of conventional formulation components. In the case of emulsifiable concentrates, the concentration of active substance can be about 1 to 80% by weight. Formulations in the form of dusts usually contain 1 to 20% by weight of active substance, sprayable solutions about 0.2 to 20% by weight of active substance. In the case of water-dispersible granules, the active substance content depends partly on whether the active compound is liquid or solid. As a rule, the water-dispersible granules contain between 10 and 90% by weight.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, soil granules or granules for broadcasting and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active substance, but is preferably between 0.01 and 5 kg/ha.

The examples which follow serve to illustrate the invention in greater detail:

A. Formulation Examples a) A dust is obtained by mixing 10 parts by weight of a compound of the formula (I) or, if appropriate, a mixture of active substance with a herbicide and 90 parts by weight of talc as the inert substance and comminuting the mixture in a hammer mill.

b) A wettable powder which is readily dispersible in water is obtained by mixing 25 parts by weight of a compound of the formula (I) or an active substance mixture of safener of the formula (I) with a herbicide, 64 parts by weight of kaolin-containing quartz as the inert substance, 10 parts by weight of potassium ligninsulfonate and 1 part by weight of sodium oleylmethyltauride as the wetting and dispersing agent, and grinding the mixture in a pinned-disk mill.

c) A dispersion concentrate which is readily dispersible in water is obtained by mixing 20 parts by weight of a compound of the formula (I), if appropriate as a mixture with a herbicide with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I) or an active substance mixture of safenet (I) and herbicide, 75 parts by weight of cyclohexanone as the solvent and 10 parts by weight of oxyethylated nonylphenol as the emulsifier.

e) Water-dispersible granules are obtained by mixing

| | |
|---|---|
| 75 parts by weight | of a compound of the formula I, if appropriate as a mixture with a herbicide, |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding the mixture in a pinned-disk mill, and granulating the powder in a fluidized bed while spraying on water as the granulation liquid.

f) Alternatively, water-dispersible granules are obtained by homogenizing and comminuting

| | |
|---|---|
| 25 parts by weight | of a compound of the formula (I) or a mixture of the compound with a herbicide, |
| 5 parts by weight | of sodium 2.2'-dinaphthylmethane-6,6'-disulfonate, |
| 2 parts by weight | of sodium oleoylmethyltaurinate, |
| 1 part by weight | of polyvinyl alcohol, |
| 17 parts by weight | of calcium carbonate and |
| 50 parts by weight | of water | in a colloid mill, subsequently grinding the mixture in a bead mill, and atomizing and drying the resulting suspension in a spray tower by means of a single-fluid jet.

B. Chemical Examples

Methyl 5-trimethylsilyl-2-isoxazoline-3-carboxylate (Table 1, Example No. 2)

3 g of vinyltrimethylsilane and 4.13 g of chloroximinomethyl acetate are introduced into 150 ml of ether, and 4.1 g of triethylamine in 150 ml of ether are then slowly added dropwise. Water is subsequently added, and the mixture is extracted several times using ether. The ether phase is dried using magnesium sulfate, concentrated on a Rotavapor and separated over a silica gel column (solvent n-heptane:ethyl acetate 9:1)

Yield: 5.1 g of the desired pure substance.

Refractive index $n_D^{20} = 1.467$

Ethyl 5-trimethylsilylmethyl-2-isoxazoline-3-carboxylate (Table 1, Example 3)

3.43 g of allyltrimethylsilane and 4.55 g of chloroximinoethyl acetate are introduced into 150 ml of ether. 3.03 g of triethylamine in 150 ml of ether are then slowly added dropwise. Water is subsequently added, and the mixture is extracted several times using ether. The ether phase is dried over $MgSO_4$, and the ether is subsequently stripped off on a Rotavapor. Separation over a silica gel column (solvent: n-heptane:ether acetate=8:2) gives 4.2 g of the desired pure substance of a refractive index $n_D^{20} - 1.462$ The Examples listed in Tables 1–6 are obtained in an analogous manner.

The analogous carboxylic acids can also be prepared from the corresponding esters, or, if desired, the esters can be prepared from the corresponding carboxylic acids, by methods known in principle.

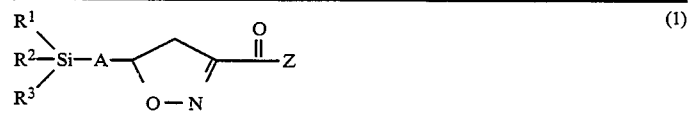

(1)

| Example | $R^1$ | $R^2$ | $R^3$ | A | Z | $Fp/n_D^{20}$ |
|---|---|---|---|---|---|---|
| 1 | $CH_3$ | $CH_3$ | $CH_3$ | $-CH_2-$ | OH | 103° C. |
| 2 | " | " | " | " | $-OCH_3$ | 1,467 |
| 3 | " | " | " | " | $-OC_2H_5$ | 1,462 |
| 4 | " | " | " | " | $-OC_3H_7$ | |
| 5 | " | " | " | " | $-O-CH(CH_3)_2$ | |
| 6 | " | " | " | " | $-OC_4H_9$ | 1,462 |
| 7 | " | " | " | " | $-OCH_2CO_2C_2H_5$ | |
| 8 | " | " | " | " | $-OC_6H_5$ | |
| 9 | " | " | " | " | $-O-CH_2C_6H_5$ | |
| 10 | " | " | " | " | $-OCH_2CH=CH_2$ | 1,4712 |
| 11 | " | " | " | " | $-OCH_2C\equiv CH$ | 1,482 |
| 12 | " | " | " | " | $-O^-Na^+$ | |
| 13 | " | " | " | " | $-OCH_2Si(CH_3)_3$ | |
| 14 | " | " | " | " | $-N(CH_3)_2$ | |
| 15 | " | " | " | " | $-O-CH(CH_3)CO_2C_2H_5$ | |
| 16 | " | " | " | " | $-NH_2$ | |
| 17 | " | " | " | " | $-O^-NH_4^+$ | |
| 18 | " | " | " | " | $-OCH_3CO_2CH_3$ | |
| 19 | " | " | " | " | $-OCH(CH_3)CO_2CH_3$ | |
| 20 | " | " | " | " | $-O^-K^+$ | |
| 21 | " | " | " | " | $-OCH_2CH(CH_3)_2$ | |

| Example | $R^1$ | $R^2$ | $R^3$ | A | Z | $n_D^{20}$ |
|---|---|---|---|---|---|---|
| 22 | $CH_3$ | $CH_3$ | $C_6H_5$ | $-CH_2-$ | OH | 1,530 |
| 23 | " | " | " | " | $-OCH_3$ | 1,5252 |
| 24 | " | " | " | " | $-OC_2H_5$ | 1,514 |
| 25 | " | " | " | " | $-OC_3H_7$ | |
| 26 | " | " | " | " | $-O-CH(CH_3)_2$ | |
| 27 | " | " | " | " | $-OC_4H_9$ | |
| 28 | " | " | " | " | $-OCH_2CO_2C_2H_5$ | |
| 29 | " | " | " | " | $-OC_6H_5$ | |
| 30 | " | " | " | " | $-O-CH_2C_6H_5$ | |

-continued

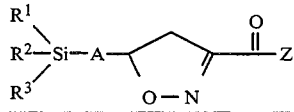

(1)

| | $R^1$ | $R^2$ | $R^3$ | A | Z |
|---|---|---|---|---|---|
| 31 | " | " | " | " | —OCH₂CH=CH₂ |
| 32 | " | " | " | " | —OCH₂C≡CH |
| 33 | " | " | " | " | —O⁻Na⁺ |
| 34 | " | " | " | " | —OCH₂Si(CH₃)₃ |
| 35 | " | " | " | " | —N(CH₃)₂ |
| 36 | " | " | " | " | —O—CH(CH₃)CO₂C₂H₅ |
| 37 | " | " | " | " | —NH₂ |
| 38 | " | " | " | " | —O⁻NH₄⁺ |
| 39 | " | " | " | " | —OCH₃CO₂CH₃ |
| 40 | " | " | " | " | —OCH(CH₃)CO₂CH₃ |
| 41 | " | " | " | " | —O⁻K⁺ |
| 42 | " | " | " | " | —OCH₂CH(CH₃)₂ |
| 43 | CH₃ | CH₃ | C₂H₅ | —CH₂— | OH |
| 44 | " | " | " | " | —OCH₃ |
| 45 | " | " | " | " | —OC₂H₅ |
| 46 | " | " | " | " | —OC₃H₇ |
| 47 | " | " | " | " | —O—CH(CH₃)₂ |
| 48 | " | " | " | " | —OC₄H₉ |
| 49 | " | " | " | " | —OCH₂CO₂C₂H₅ |
| 50 | " | " | " | " | —OC₆H₅ |
| 51 | " | " | " | " | —O—CH₂C₆H₅ |
| 52 | " | " | " | " | —OCH₂CH=CH₂ |
| 53 | " | " | " | " | —OCH₂C≡CH |
| 54 | " | " | " | " | —O⁻Na⁺ |
| 55 | " | " | " | " | —OCH₂Si(CH₃)₃ |
| 56 | " | " | " | " | —N(CH₃)₂ |
| 57 | " | " | " | " | —O—CH(CH₃)CO₂C₂H₅ |
| 58 | " | " | " | " | —NH₂ |
| 59 | " | " | " | " | —O⁻NH₄⁺ |
| 60 | " | " | " | " | —OCH₃CO₂CH₃ |
| 61 | " | " | " | " | —OCH(CH₃)CO₂CH₃ |
| 62 | " | " | " | " | —O⁻K⁺ |
| 63 | " | " | " | " | —OCH₂CH(CH₃)₂ |
| 64 | CH₃ | CH₃ | C₂H₅ | —CH₂— | OH |
| 65 | " | " | " | " | —OCH₃ |
| 66 | " | " | " | " | —OC₂H₅ |
| 67 | " | " | " | " | —OC₃H₇ |
| 68 | " | " | " | " | —O—CH(CH₃)₂ |
| 69 | " | " | " | " | —OC₄H₉ |
| 70 | " | " | " | " | —OCH₂CO₂C₂H₅ |
| 71 | " | " | " | " | —OC₆H₅ |
| 72 | " | " | " | " | —O—CH₂C₆H₅ |
| 73 | " | " | " | " | —OCH₂CH=CH₂ |
| 74 | " | " | " | " | —OCH₂C≡CH |
| 75 | " | " | " | " | —O⁻Na⁺ |
| 76 | " | " | " | " | —OCH₂Si(CH₃)₃ |
| 77 | " | " | " | " | —N(CH₃)₂ |
| 78 | " | " | " | " | —O—CH(CH₃)CO₂C₂H₅ |
| 79 | " | " | " | " | —NH₂ |
| 80 | " | " | " | " | —O⁻NH₄⁺ |
| 81 | " | " | " | " | —OCH₃CO₂CH₃ |
| 82 | " | " | " | " | —OCH(CH₃)CO₂CH₃ |
| 83 | " | " | " | " | —O⁻K⁺ |
| 84 | " | " | " | " | —OCH₂CH(CH₃)₂ |
| 85 | —CH(CH₃)₂ | —CH(CH₃)₂ | —CH(CH₃)₂ | —CH₂— | OH |
| 86 | " | " | " | " | —OCH₃ |
| 87 | " | " | " | " | —OC₂H₅ |
| 88 | " | " | " | " | —OC₃H₇ |
| 89 | " | " | " | " | —O—CH(CH₃)₂ |
| 90 | " | " | " | " | —OC₄H₉ |
| 91 | " | " | " | " | —OCH₂CO₂C₂H₅ |
| 92 | " | " | " | " | —OC₆H₅ |
| 93 | " | " | " | " | —O—CH₂C₆H₅ |
| 94 | " | " | " | " | —O—CH₂CH=CH₂ |
| 95 | " | " | " | " | —OCH₂C≡CH |
| 96 | " | " | " | " | —O⁻Na⁺ |
| 97 | " | " | " | " | —OCH₂Si(CH₃)₃ |
| 98 | " | " | " | " | —N(CH₃)₂ |
| 99 | " | " | " | " | —O—CH(CH₃)CO₂C₂H₅ |
| 100 | " | " | " | " | —NH₂ |
| 101 | " | " | " | " | —O⁻NH₄⁺ |
| 102 | " | " | " | " | —OCH₂Cl₂CH₃ |
| 103 | " | " | " | " | —OCH(CH₃)CO₂CH₃ |
| 104 | " | " | " | " | —O⁻K⁺ |
| 105 | " | " | " | " | —OCH₂CH(CH₃)₂ |
| 106 | C₆H₅ | C₆H₅ | C₆H₅ | CH₂ | OH |
| 107 | " | " | " | " | —OCH₃ |

-continued

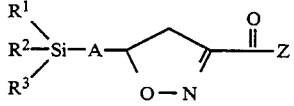

(1)

| | $R^1$ | $R^2$ | $R^3$ | A | Z |
|---|---|---|---|---|---|
| 108 | " | " | " | " | $-OC_2H_5$ |
| 109 | " | " | " | " | $-OC_3H_7$ |
| 110 | " | " | " | " | $-O-CH(CH_3)_2$ |
| 111 | " | " | " | " | $-OC_4H_9$ |
| 112 | " | " | " | " | $-OCH_2CO_2C_2H_5$ |
| 113 | " | " | " | " | $-OC_6H_5$ |
| 114 | " | " | " | " | $-O-CH_2C_6H_5$ |
| 115 | " | " | " | " | $-OCH_2CH=CH_2$ |
| 116 | " | " | " | " | $-OCH_2C\equiv CH$ |
| 117 | " | " | " | " | $-O^-Na^+$ |
| 118 | " | " | " | " | $-OCH_2Si(CH_3)_3$ |
| 119 | " | " | " | " | $-N(CH_3)_2$ |
| 120 | " | " | " | " | $-O-CH(CH_3)CO_2C_2H_5$ |
| 121 | " | " | " | " | $-NH_2$ |
| 122 | " | " | " | " | $-O^-NH_4^+$ |
| 123 | " | " | " | " | $-OCH_3CO_2CH_3$ |
| 124 | " | " | " | " | $-OCH(CH_3)CO_2CH_3$ |
| 125 | " | " | " | " | $-O^-K^+$ |
| 126 | " | " | " | " | $-OCH_2CH(CH_3)_2$ |
| 127 | $CH_3$ | $CH_3$ | $(t)C_4H_9$ | $CH_2$ | OH |
| 128 | " | " | " | " | $-OCH_3$ |
| 129 | " | " | " | " | $-OC_2H_5$ |
| 130 | " | " | " | " | $-OC_3H_7$ |
| 131 | " | " | " | " | $-O-CH(CH_3)_2$ |
| 132 | " | " | " | " | $-OC_4H_9$ |
| 133 | " | " | " | " | $-OCH_2CO_2C_2H_5$ |
| 134 | " | " | " | " | $-OC_6H_5$ |
| 135 | " | " | " | " | $-O-CH_2C_6H_5$ |
| 136 | " | " | " | " | $-OCH_2CH=CH_2$ |
| 137 | " | " | " | " | $-OCH_2C\equiv CH$ |
| 138 | " | " | " | " | $-O^-Na^+$ |
| 139 | " | " | " | " | $-OCH_2Si(CH_3)_3$ |
| 140 | " | " | " | " | $-N(CH_3)_2$ |
| 141 | " | " | " | " | $-O-CH(CH_3)CO_2C_2H_5$ |
| 142 | " | " | " | " | $-NH_2$ |
| 143 | " | " | " | " | $-O^-NH_4^+$ |
| 144 | " | " | " | " | $-OCH_3CO_2CH_3$ |
| 145 | " | " | " | " | $-OCH(CH_3)CO_2CH_3$ |
| 146 | " | " | " | " | $-O^-K^+$ |
| 147 | " | " | " | " | $-OCH_2CH(CH_3)_2$ |
| 148 | $(n)C_6H_{13}$ | $(n)C_6H_{13}$ | $(n)C_6H_{13}$ | $CH_2$ | OH |
| 149 | " | " | " | " | $-OCH_3$ |
| 150 | " | " | " | " | $-OC_2H_5$ |
| 151 | " | " | " | " | $-OC_3H_7$ |
| 152 | " | " | " | " | $-O-CH(CH_3)_2$ |
| 153 | " | " | " | " | $-OC_4H_9$ |
| 154 | " | " | " | " | $-OCH_2CO_2C_2H_5$ |
| 155 | " | " | " | " | $-OC_6H_5$ |
| 156 | " | " | " | " | $-O-CH_2C_6H_5$ |
| 157 | " | " | " | " | $-O-CH_2CH=CH_2$ |
| 158 | " | " | " | " | $-OCH_2C\equiv CH$ |
| 159 | " | " | " | " | $-O^-Na^+$ |
| 160 | " | " | " | " | $-OCH_2Si(CH_3)_3$ |
| 161 | " | " | " | " | $-N(CH_3)_2$ |
| 162 | " | " | " | " | $-O-CH(CH_3)CO_2C_2H_5$ |
| 163 | " | " | " | " | $-NH_2$ |
| 164 | " | " | " | " | $-O^-NH_4^+$ |
| 165 | " | " | " | " | $-OCH_2Cl_2CH_3$ |
| 166 | " | " | " | " | $-OCH(CH_3)CO_2CH_3$ |
| 167 | " | " | " | " | $-O^-K^+$ |
| 168 | " | " | " | " | $-OCH_2CH(CH_3)_2$ |
| 169 | $(iso)C_4H_9$ | $(iso)C_4H_9$ | $(iso)C_4H_9$ | $-CH_2-$ | OH |
| 170 | " | " | " | " | $-OCH_3$ |
| 171 | " | " | " | " | $-OC_2H_5$ |
| 172 | " | " | " | " | $-OC_3H_7$ |
| 173 | " | " | " | " | $-O-CH(CH_3)_2$ |
| 174 | " | " | " | " | $-OC_4H_9$ |
| 175 | " | " | " | " | $-OCH_2CO_2C_2H_5$ |
| 176 | " | " | " | " | $-OC_6H_5$ |
| 177 | " | " | " | " | $-O-CH_2C_6H_5$ |
| 178 | " | " | " | " | $-O-CH_2CH=CH_2$ |
| 179 | " | " | " | " | $-OCH_2C\equiv CH$ |
| 180 | " | " | " | " | $-O^-Na^+$ |
| 181 | " | " | " | " | $-OCH_2Si(CH_3)_3$ |
| 182 | " | " | " | " | $-N(CH_3)_2$ |
| 183 | " | " | " | " | $-O-CH(CH_3)CO_2C_2H_5$ |
| 184 | " | " | " | " | $-NH_2$ |

-continued $$\begin{array}{c} R^1 \\ R^2-Si-A-\overset{|}{\underset{O-N}{C}}=\overset{O}{\overset{\|}{C}}-Z \end{array} \quad (1)$$

| | $R^1$ | $R^2$ | $R^3$ | A | Z | |
|---|---|---|---|---|---|---|
| 185 | " | " | " | " | $-O^-NH_4^+$ | |
| 186 | " | " | " | " | $-OCH_2Cl_2CH_3$ | |
| 187 | " | " | " | " | $-OCH(CH_3)CO_2CH_3$ | |
| 188 | " | " | " | " | $-O^-K^+$ | |
| 189 | " | " | " | " | $-OCH_2CH(CH_3)_2$ | |
| 190 | $(n)C_3H_7$ | $(n)C_3H_7$ | $(n)C_3H_7$ | $CH_2$ | OH | |
| 191 | " | " | " | " | $-OCH_3$ | |
| 192 | " | " | " | " | $-OC_2H_5$ | |
| 193 | " | " | " | " | $-OC_3H_7$ | |
| 194 | " | " | " | " | $-O-CH(CH_3)_2$ | |
| 195 | " | " | " | " | $-OC_4H_9$ | |
| 196 | " | " | " | " | $-OCH_2CO_2C_2H_5$ | |
| 197 | " | " | " | " | $-OC_6H_5$ | |
| 198 | " | " | " | " | $-O-CH_2C_6H_5$ | |
| 199 | " | " | " | " | $-O-CH_2CH=CH_2$ | |
| 200 | " | " | " | " | $-OCH_2C\equiv CH$ | |
| 201 | " | " | " | " | $-O^-Na^+$ | |
| 202 | " | " | " | " | $-OCH_2Si(CH_3)_3$ | |
| 203 | " | " | " | " | $-N(CH_3)_2$ | |
| 204 | " | " | " | " | $-O-CH(CH_3)CO_2C_2H_5$ | |
| 205 | " | " | " | " | $-NH_2$ | |
| 206 | " | " | " | " | $-O^-NH_4^+$ | |
| 207 | " | " | " | " | $-OCH_2Cl_2CH_3$ | |
| 208 | " | " | " | " | $-OCH(CH_3)CO_2CH_3$ | |
| 209 | " | " | " | " | $-O^-K^+$ | |
| 210 | " | " | " | " | $-OCH_2CH(CH_3)_2$ | |
| 211 | $CH_3$ | $CH_3$ | $(iso)C_3H_7$ | $CH_2$ | $OCH_3$ | 1,4709 |
| 212 | " | " | " | " | $OC_2H_5$ | 1,4693 |
| 213 | " | " | $-C(CH_3)_2CH(CH_3)_2$ | " | $OCH_3$ | |
| 214 | " | " | " | " | $OC_2H_5$ | |
| 215 | $-CH_2C_6H_5$ | $CH_2C_6H_5$ | $CH_2C_6H_5$ | " | $OCH_3$ | |
| 216 | " | " | " | " | $OC_2H_5$ | |
| 217 | $(n)C_4H_9$ | $(n)C_4H_9$ | $(n)C_4H_9$ | " | $OCH_3$ | |
| 218 | " | " | " | " | $OC_2H_5$ | |
| 219 | " | " | " | " | OH | |
| 220 | $CH_3$ | $CH_3$ | $(n)C_8H_{17}$ | " | OH | |
| 221 | " | " | " | " | $OCH_3$ | |
| 222 | " | " | " | " | $OC_2H_5$ | |
| 223 | " | " | $-CH_2C_6H_5$ | " | OH | |
| 224 | " | " | " | " | $OCH_3$ | |
| 225 | " | " | " | " | $OC_2H_5$ | |
| 226 | " | " | $(n)C_{18}H_{37}$ | " | OH | |
| 227 | " | " | " | " | $OCH_3$ | wax |
| 228 | " | " | " | " | $OC_2H_5$ | wax |
| 229 | " | " | $(n)C_{10}H_{21}$ | " | OH | |
| 230 | " | " | " | " | $OCH_3$ | |
| 231 | " | " | " | " | $OC_2H_5$ | |
| 232 | $CH_3$ | $CH_3$ | $-CH_2CH_2C(CH_3)_2CH_3$ | $CH_2$ | OH | |
| 233 | " | " | " | " | $OCH_3$ | |
| 234 | " | " | " | " | $OC_2H_5$ | |
| 235 | " | " | $(iso)C_3H_7$ | " | OH | |
| 236 | " | " | $C(CH_3)_2CH(CH_3)_2$ | " | OH | |
| 237 | $CH_2C_6H_5$ | $CH_2C_6H_5$ | $CH_2C_6H_5$ | " | OH | |
| 238 | $CH_3$ | $C_2H_5$ | $C_2H_5$ | " | OH | |
| 239 | " | " | " | " | $OCH_3$ | |
| 240 | " | " | " | " | $OC_2H_5$ | |
| 241 | $CH_3$ | $CH_3$ | $(n)C_3H_7$ | " | OH | |
| 242 | " | " | " | " | $OCH_3$ | |
| 243 | " | " | " | " | $OC_2H_5$ | |
| 244 | $CH_3$ | $(n)C_3H_7$ | $(n)C_3H_7$ | " | OH | |
| 245 | " | " | " | " | $OCH_3$ | |
| 246 | " | " | " | " | $OC_2H_5$ | |
| 247 | $CH_3$ | $isoC_3H_7$ | $isoC_3H_7$ | " | OH | |
| 248 | " | " | " | " | $OCH_3$ | |
| 249 | " | " | " | " | $OC_2H_5$ | |
| 250 | $CH_3$ | $CH_3$ | $n-C_4H_9$ | " | OH | |
| 251 | " | " | " | " | $OCH_3$ | |
| 252 | " | " | " | " | $OC_2H_5$ | |
| 253 | " | $nC_4H_9$ | $n-C_4H_9$ | " | OH | |
| 254 | " | " | " | " | $OCH_3$ | |
| 255 | " | " | " | " | $OC_2H_5$ | |
| 256 | $CH_3$ | $C_6H_5$ | $C_6H_5$ | " | OH | |
| 257 | " | " | " | " | $OCH_3$ | |
| 258 | " | " | " | " | $OC_2H_5$ | |

TABLE 2

$$\text{(structure shown: } R^1R^2R^3Si\text{-CH-CH}_2\text{-C(=N-O-)-C(=O)-Z\text{ isoxazoline ring)}$$ (2)

| Example | R¹ | R² | R³ | Z | $n_D^{20}$ |
|---|---|---|---|---|---|
| 259 | CH₃ | CH₃ | CH₃ | OH | |
| 260 | " | " | " | —OCH₃ | 1,466 |
| 261 | " | " | " | —OC₂H₅ | 1,463 |
| 262 | " | " | " | —OC₃H₇ | |
| 263 | " | " | " | —O—CH(CH₃)₂ | |
| 264 | " | " | " | —OC₄H₉ | |
| 265 | " | " | " | —OCH₂CO₂C₂H₅ | |
| 266 | " | " | " | —OC₆H₅ | |
| 267 | " | " | " | —O—CH₂C₆H₅ | |
| 268 | " | " | " | —OCH₂CH=CH₂ | |
| 269 | " | " | " | —OCH₂C≡CH | |
| 270 | " | " | " | —O⁻Na⁺ | |
| 271 | " | " | " | —OCH₂Si(CH₃)₃ | |
| 272 | " | " | " | —N(CH₃)₂ | |
| 273 | " | " | " | —O—CH(CH₃)CO₂C₂H₅ | |
| 274 | " | " | " | —NH₂ | |
| 275 | " | " | " | —O⁻NH₄⁺ | |
| 276 | " | " | " | —OCH₃CO₂CH₃ | |
| 277 | " | " | " | —OCH(CH₃)CO₂CH₃ | |
| 278 | " | " | " | —O⁻K⁺ | |
| 279 | " | " | " | —OCH₂CH(CH₃)₂ | |
| 280 | CH₃ | CH₃ | C₆H₅ | OH | |
| 281 | " | " | " | —OCH₃ | |
| 282 | " | " | " | —OC₂H₅ | |
| 283 | " | " | " | —OC₃H₇ | |
| 284 | " | " | " | —O—CH(CH₃)₂ | |
| 285 | " | " | " | —OC₄H₉ | |
| 286 | " | " | " | —OCH₂CO₂C₂H₅ | |
| 287 | " | " | " | —OC₆H₅ | |
| 288 | " | " | " | —O—CH₂C₆H₅ | |
| 289 | " | " | " | —OCH₂CH=CH₂ | |
| 290 | " | " | " | —OCH₂C≡CH | |
| 291 | " | " | " | —O⁻Na⁺ | |
| 292 | " | " | " | —OCH₂Si(CH₃)₃ | |
| 293 | " | " | " | —N(CH₃)₂ | |
| 294 | " | " | " | —O—CH(CH₃)CO₂C₂H₅ | |
| 295 | " | " | " | —NH₂ | |
| 296 | " | " | " | —O⁻NH₄⁺ | |
| 297 | " | " | " | —OCH₃CO₂CH₃ | |
| 298 | " | " | " | —OCH(CH₃)CO₂CH₃ | |
| 299 | " | " | " | —O⁻K⁺ | |
| 300 | " | " | " | —OCH₂CH(CH₃)₂ | |
| 301 | CH₃ | CH₃ | C₆H₅ | OH | |
| 302 | " | " | " | —OCH₃ | |
| 303 | " | " | " | —OC₂H₅ | |
| 304 | " | " | " | —OC₃H₇ | |
| 305 | " | " | " | —O—CH(CH₃)₂ | |
| 306 | " | " | " | —OC₄H₉ | |
| 307 | " | " | " | —OCH₂CO₂C₂H₅ | |
| 308 | " | " | " | —OC₆H₅ | |
| 309 | " | " | " | —O—CH₂C₆H₅ | |
| 310 | " | " | " | —OCH₂CH=CH₂ | |
| 311 | " | " | " | —OCH₂C≡CH | |
| 312 | " | " | " | —O⁻Na⁺ | |
| 313 | " | " | " | —OCH₂Si(CH₃)₃ | |
| 314 | " | " | " | —N(CH₃)₂ | |
| 315 | " | " | " | —O—CH(CH₃)CO₂C₂H₅ | |
| 316 | " | " | " | —NH₂ | |
| 317 | " | " | " | —O⁻NH₄⁺ | |
| 318 | " | " | " | —OCH₃CO₂CH₃ | |
| 319 | " | " | " | —OCH(CH₃)CO₂CH₃ | |
| 320 | " | " | " | —O⁻K⁺ | |
| 321 | " | " | " | —OCH₂CH(CH₃)₂ | |
| 322 | C₂H₅ | C₂H₅ | C₆H₅ | OH | |
| 323 | " | " | " | —OCH₃ | |
| 324 | " | " | " | —OC₂H₅ | |
| 325 | " | " | " | —OC₃H₇ | |
| 326 | " | " | " | —O—CH(CH₃)₂ | |
| 327 | " | " | " | —OC₄H₉ | |
| 328 | " | " | " | —OCH₂CO₂C₂H₅ | |
| 329 | " | " | " | —OC₆H₅ | |
| 330 | " | " | " | —O—CH₂C₆H₅ | |
| 331 | " | " | " | —OCH₂CH=CH₂ | |
| 332 | " | " | " | —OCH₂C≡CH | |
| 333 | " | " | " | —O⁻Na⁺ | |

TABLE 2-continued $$\underset{R^3}{\overset{R^1}{\underset{|}{R^2-Si}}}-\underset{O-N}{\overset{}{C}}\overset{O}{\underset{\parallel}{C}}-Z \quad (2)$$

| Example | $R^1$ | $R^2$ | $R^3$ | Z | $n_D^{20}$ |
|---|---|---|---|---|---|
| 334 | " | " | " | —OCH$_2$Si(CH$_3$)$_3$ | |
| 335 | " | " | " | —N(CH$_3$)$_2$ | |
| 336 | " | " | " | —O—CH(CH$_3$)CO$_2$C$_2$H$_5$ | |
| 337 | " | " | " | —NH$_2$ | |
| 338 | " | " | " | —O$^-$NH$_4^+$ | |
| 339 | " | " | " | —OCH$_3$CO$_2$CH$_3$ | |
| 340 | " | " | " | —OCH(CH$_3$)CO$_2$CH$_3$ | |
| 341 | " | " | " | —O$^-$K$^+$ | |
| 342 | " | " | " | —OCH$_2$CH(CH$_3$)$_2$ | |
| 343 | —CH(CH$_3$)$_2$ | —CH(CH$_3$)$_2$ | —CH(CH$_3$)$_2$ | OH | |
| 344 | " | " | " | —OCH$_3$ | |
| 345 | " | " | " | —OC$_2$H$_5$ | |
| 346 | " | " | " | —OC$_3$H$_7$ | |
| 347 | " | " | " | —O—CH(CH$_3$)$_2$ | |
| 348 | " | " | " | —OC$_4$H$_9$ | |
| 349 | " | " | " | —OCH$_2$CO$_2$C$_2$H$_5$ | |
| 350 | " | " | " | —OC$_6$H$_5$ | |
| 351 | " | " | " | —O—CH$_2$C$_6$H$_5$ | |
| 352 | " | " | " | —O—CH$_2$CH=CH$_2$ | |
| 353 | " | " | " | —OCH$_2$C≡CH | |
| 354 | " | " | " | —O$^-$Na$^+$ | |
| 355 | " | " | " | —OCH$_2$Si(CH$_3$)$_3$ | |
| 356 | " | " | " | —N(CH$_3$)$_2$ | |
| 357 | " | " | " | —O—CH(CH$_3$)CO$_2$C$_2$H$_5$ | |
| 358 | " | " | " | —NH$_2$ | |
| 359 | " | " | " | —O$^-$NH$_4^+$ | |
| 360 | " | " | " | —OCH$_2$Cl$_2$CH$_3$ | |
| 361 | " | " | " | —OCH(CH$_3$)CO$_2$CH$_3$ | |
| 362 | " | " | " | —O$^-$K$^+$ | |
| 363 | " | " | " | —OCH$_2$CH(CH$_3$)$_2$ | |
| 364 | C$_6$H$_5$ | C$_6$H$_5$ | C$_6$H$_5$ | OH | |
| 365 | " | " | " | —OCH$_3$ | |
| 366 | " | " | " | —OC$_2$H$_5$ | |
| 367 | " | " | " | —OC$_3$H$_7$ | |
| 368 | " | " | " | —O—CH(CH$_3$)$_2$ | |
| 369 | " | " | " | —OC$_4$H$_9$ | |
| 370 | " | " | " | —OCH$_2$CO$_2$C$_2$H$_5$ | |
| 371 | " | " | " | —OC$_6$H$_5$ | |
| 372 | " | " | " | —O—CH$_2$C$_6$H$_5$ | |
| 373 | " | " | " | —OCH$_2$CH=CH$_2$ | |
| 374 | " | " | " | —OCH$_2$C≡CH | |
| 375 | " | " | " | —O$^-$Na$^+$ | |
| 376 | " | " | " | —OCH$_2$Si(CH$_3$)$_3$ | |
| 377 | " | " | " | —N(CH$_3$)$_2$ | |
| 378 | " | " | " | —O—CH(CH$_3$)CO$_2$C$_2$H$_5$ | |
| 379 | " | " | " | —NH$_2$ | |
| 380 | " | " | " | —O$^-$NH$_4^+$ | |
| 381 | " | " | " | —OCH$_3$CO$_2$CH$_3$ | |
| 382 | " | " | " | —OCH(CH$_3$)CO$_2$CH$_3$ | |
| 383 | " | " | " | —O$^-$K$^+$ | |
| 384 | " | " | " | —OCH$_2$CH(CH$_3$)$_2$ | |
| 385 | CH$_3$ | CH$_3$ | (t)-C$_4$H$_9$ | OH | |
| 386 | " | " | " | —OCH$_3$ | |
| 387 | " | " | " | —OC$_2$H$_5$ | |
| 388 | " | " | " | —OC$_3$H$_7$ | |
| 389 | " | " | " | —O—CH(CH$_3$)$_2$ | |
| 390 | " | " | " | —OC$_4$H$_9$ | |
| 391 | " | " | " | —OCH$_2$CO$_2$C$_2$H$_5$ | |
| 392 | " | " | " | —OC$_6$H$_5$ | |
| 393 | " | " | " | —O—CH$_2$C$_6$H$_5$ | |
| 394 | " | " | " | —OCH$_2$CH=CH$_2$ | |
| 395 | " | " | " | —OCH$_2$C≡CH | |
| 396 | " | " | " | —O$^-$Na$^+$ | |
| 397 | " | " | " | —OCH$_2$Si(CH$_3$)$_3$ | |
| 398 | " | " | " | —N(CH$_3$)$_2$ | |
| 399 | " | " | " | —O—CH(CH$_3$)CO$_2$C$_2$H$_5$ | |
| 400 | " | " | " | —NH$_2$ | |
| 401 | " | " | " | —O$^-$NH$_4^+$ | |
| 402 | " | " | " | —OCH$_3$CO$_2$CH$_3$ | |
| 403 | " | " | " | —OCH(CH$_3$)CO$_2$CH$_3$ | |
| 404 | " | " | " | —O$^-$K$^+$ | |
| 405 | " | " | " | —OCH$_2$CH(CH$_3$)$_2$ | |
| 406 | (n)C$_6$H$_{13}$ | (n)C$_6$H$_{13}$ | (n)C$_6$H$_{13}$ | OH | |
| 407 | " | " | " | —OCH$_3$ | |
| 408 | " | " | " | —OC$_2$H$_5$ | |

TABLE 2-continued $$\begin{array}{c} R^1 \\ R^2-Si- \\ R^3 \end{array} \begin{array}{c} \\ \\ O-N \end{array} \begin{array}{c} O \\ \| \\ -Z \end{array} \quad (2)$$

| Example | R¹ | R² | R³ | Z | $n_D^{20}$ |
|---|---|---|---|---|---|
| 409 | " | " | " | —OC₃H₇ | |
| 410 | " | " | " | —O—CH(CH₃)₂ | |
| 411 | " | " | " | —OC₄H₉ | |
| 412 | " | " | " | —OCH₂CO₂C₂H₅ | |
| 413 | " | " | " | —OC₆H₅ | |
| 414 | " | " | " | —O—CH₂C₆H₅ | |
| 415 | " | " | " | —O—CH₂CH=CH₂ | |
| 416 | " | " | " | —OCH₂C≡CH | |
| 417 | " | " | " | —O⁻Na⁺ | |
| 418 | " | " | " | —OCH₂Si(CH₃)₃ | |
| 419 | " | " | " | —N(CH₃)₂ | |
| 420 | " | " | " | —O—CH(CH₃)CO₂C₂H₅ | |
| 421 | " | " | " | —NH₂ | |
| 422 | " | " | " | —O⁻NH₄⁺ | |
| 423 | " | " | " | —OCH₂Cl₂CH₃ | |
| 424 | " | " | " | —OCH(CH₃)CO₂CH₃ | |
| 425 | " | " | " | —O⁻K⁺ | |
| 426 | " | " | " | —OCH₂CH(CH₃)₂ | |
| 427 | (iso)C₄H₉ | (iso)C₄H₉ | (iso)C₄H₉ | OH | |
| 428 | " | " | " | —OCH₃ | |
| 429 | " | " | " | —OC₂H₅ | |
| 430 | " | " | " | —OC₃H₇ | |
| 431 | " | " | " | —O—CH(CH₃)₂ | |
| 432 | " | " | " | —OC₄H₉ | |
| 433 | " | " | " | —OCH₂CO₂C₂H₅ | |
| 434 | " | " | " | —OC₆H₅ | |
| 435 | " | " | " | —O—CH₂C₆H₅ | |
| 436 | " | " | " | —O—CH₂CH=CH₂ | |
| 437 | " | " | " | —OCH₂C≡CH | |
| 438 | " | " | " | —O⁻Na⁺ | |
| 439 | " | " | " | —OCH₂Si(CH₃)₃ | |
| 440 | " | " | " | —N(CH₃)₂ | |
| 441 | " | " | " | —O—CH(CH₃)CO₂C₂H₅ | |
| 442 | " | " | " | —NH₂ | |
| 443 | " | " | " | —O⁻NH₄⁺ | |
| 444 | " | " | " | —OCH₂Cl₂CH₃ | |
| 445 | " | " | " | —OCH(CH₃)CO₂CH₃ | |
| 446 | " | " | " | —O⁻K⁺ | |
| 447 | " | " | " | —OCH₂CH(CH₃)₂ | |
| 448 | (n)C₃H₇ | (n)C₃H₇ | (n)C₃H₇ | OH | |
| 449 | " | " | " | —OCH₃ | |
| 450 | " | " | " | —OC₂H₅ | |
| 451 | " | " | " | —OC₃H₇ | |
| 452 | " | " | " | —O—CH(CH₃)₂ | |
| 453 | " | " | " | —OC₄H₉ | |
| 454 | " | " | " | —OCH₂CO₂C₂H₅ | |
| 455 | " | " | " | —OC₆H₅ | |
| 456 | " | " | " | —O—CH₂C₆H₅ | |
| 457 | " | " | " | —O—CH₂CH=CH₂ | |
| 458 | " | " | " | —OCH₂C≡CH | |
| 459 | " | " | " | —O⁻Na⁺ | |
| 460 | " | " | " | —OCH₂Si(CH₃)₃ | |
| 461 | " | " | " | —N(CH₃)₂ | |
| 462 | " | " | " | —O—CH(CH₃)CO₂C₂H₅ | |
| 463 | " | " | " | —NH₂ | |
| 464 | " | " | " | —O⁻NH₄⁺ | |
| 465 | " | " | " | —OCH₂Cl₂CH₃ | |
| 466 | " | " | " | —OCH(CH₃)CO₂CH₃ | |
| 467 | " | " | " | —O⁻K⁺ | |
| 468 | " | " | " | —OCH₂CH(CH₃)₂ | |
| 469 | CH₃ | CH₃ | (iso)C₃H₇ | OCH₃ | |
| 470 | " | " | " | OC₂H₅ | |
| 471 | " | " | —C(CH₃)₂CH(CH₃)₂ | OCH₃ | |
| 472 | " | " | " | OC₂H₅ | |
| 473 | —CH₂C₆H₅ | CH₂C₆H₅ | CH₂C₆H₅ | OCH₃ | |
| 474 | " | " | " | OC₂H₅ | |
| 475 | (n)C₄H₉ | (n)C₄H₉ | (n)C₄H₉ | OCH₃ | |
| 476 | " | " | " | OC₂H₅ | |
| 477 | " | " | " | OH | |
| 478 | CH₃ | CH₃ | (n)C₈H₁₇ | OH | |
| 479 | " | " | " | OCH₃ | |
| 480 | " | " | " | OC₂H₅ | |
| 481 | " | " | —CH₂C₆H₅ | OH | |
| 482 | " | " | " | OCH₃ | |
| 483 | " | " | " | OC₂H₅ | |

TABLE 2-continued $$\begin{array}{c} R^1 \\ R^2-Si- \\ R^3 \end{array} \underset{O-N}{\overset{}{\bigotimes}} \overset{O}{\underset{}{\overset{\parallel}{C}}}-Z \quad (2)$$

| Example | $R^1$ | $R^2$ | $R^3$ | Z | $n_D^{20}$ |
|---|---|---|---|---|---|
| 484 | " | " | (n)$C_{18}H_{37}$ | OH | |
| 485 | " | " | " | $OCH_3$ | |
| 486 | " | " | " | $OC_2H_5$ | |
| 487 | " | " | (n)$C_{10}H_{21}$ | OH | |
| 488 | " | " | " | $OCH_3$ | |
| 489 | " | " | " | $OC_2H_5$ | |
| 490 | $CH_3$ | $CH_3$ | $-CH_2CH_2C(CH_3)_2CH_3$ | OH | |
| 491 | " | " | " | $OCH_3$ | |
| 492 | " | " | " | $OC_2H_5$ | |
| 493 | " | " | (iso)$C_3H_7$ | OH | |
| 494 | " | " | $C(CH_3)_2CH(CH_3)_2$ | OH | |
| 495 | $CH_2C_6H_5$ | $CH_2C_6H_5$ | $CH_2C_6H_5$ | OH | |
| 496 | $CH_3$ | $C_2H_5$ | $C_2H_5$ | OH | |
| 497 | " | " | " | $OCH_3$ | |
| 498 | " | " | " | $OC_2H_5$ | |
| 499 | $CH_3$ | $CH_3$ | (n)$C_3H_7$ | OH | |
| 500 | " | " | " | $OCH_3$ | |
| 501 | " | " | " | $OC_2H_5$ | |
| 502 | $CH_3$ | (n)$C_3H_7$ | (n)$C_3H_7$ | OH | |
| 503 | " | " | " | $OCH_3$ | |
| 504 | " | " | " | $OC_2H_5$ | |
| 505 | $CH_3$ | iso$C_3H_7$ | iso$C_3H_7$ | OH | |
| 506 | " | " | " | $OCH_3$ | |
| 507 | " | " | " | $OC_2H_5$ | |
| 508 | $CH_3$ | $CH_3$ | n-$C_4H_9$ | OH | |
| 509 | " | " | " | $OCH_3$ | |
| 510 | " | " | " | $OC_2H_5$ | |
| 511 | " | n$C_4H_9$ | n-$C_4H_9$ | OH | |
| 512 | " | " | " | $OCH_3$ | |
| 513 | " | " | " | $OC_2H_5$ | |
| 514 | $CH_3$ | $C_6H_5$ | $C_6H_5$ | OH | |
| 515 | " | " | " | $OCH_3$ | |
| 516 | " | " | " | $OC_2H_5$ | |

TABLE 3

$$\begin{array}{c} R^1 \\ R^2-Si-A \\ R^3 \end{array} \underset{X-N}{\overset{}{\bigotimes}} -B-COZ \quad (3)$$

| Example | $R^1$ | $R^2$ | $R^3$ | X | A | B | Z |
|---|---|---|---|---|---|---|---|
| 421 | $CH_3$ | $CH_3$ | $CH_3$ | O | — | $CH_2$ | $-OCH_3$ |
| 422 | " | " | " | " | " | " | $-OC_2H_5$ |
| 423 | " | " | " | " | $CH_2$ | " | $-OCH_3$ |
| 424 | " | " | " | " | " | " | $-OC_2H_5$ |
| 425 | " | " | " | " | — | $-CH_2CH_2-$ | $-OC_2H_5$ |
| 426 | " | " | " | " | $CH_2$ | " | $-OC_2H_5$ |
| 427 | " | " | " | " | " | " | $-OCH_3$ |
| 428 | " | " | " | S | $CH_2$ | — | $-OCH_3$ |
| 429 | " | " | " | " | " | " | $-OC_2H_5$ |
| 430 | " | " | " | " | — | — | $-OCH_3$ |
| 431 | " | " | " | " | " | " | $-OC_2H_5$ |
| 432 | " | " | " | " | — | $CH_2$ | $-OCH_3$ |
| 433 | " | " | " | " | — | $CH_2$ | $-OC_2H_5$ |
| 434 | " | " | " | O | $CH_2CH_2$ | — | $-OCH_3$ |
| 435 | " | " | " | " | " | — | $-OC_2H_5$ |
| 436 | " | " | " | " | " | $CH_2$ | $-OCH_3$ |
| 437 | " | " | " | " | " | $CH_2$ | $-OC_2H_5$ |

TABLE 4

$$\begin{array}{c} R^1 \\ R^2-Si-A \\ R^3 \end{array} \underset{N-X}{\overset{}{\bigotimes}} -B-COZ \quad (4)$$

| Example | $R^1$ | $R^2$ | $R^3$ | A | B | X | Z |
|---|---|---|---|---|---|---|---|
| 438 | $CH_3$ | $CH_3$ | $CH_3$ | — | — | O | $-OCH_3$ |
| 439 | " | " | " | " | " | " | $-OC_2H_5$ |
| 440 | " | " | " | $CH_2$ | — | O | $-OCH_3$ |
| 441 | " | " | " | " | " | " | $-OC_2H_5$ |
| 442 | " | " | " | " | $CH_2$ | " | $-OCH_3$ |
| 443 | " | " | " | " | " | " | $-OC_2H_5$ |
| 444 | " | " | " | — | $CH_2$ | " | $-OCH_3$ |
| 445 | " | " | " | — | $CH_2$ | " | $-OC_2H_5$ |
| 446 | " | " | " | — | — | S | $-OCH_3$ |
| 447 | " | " | " | " | " | " | $-OC_2H_5$ |
| 448 | " | " | " | $CH_2$ | — | " | $-OCH_3$ |
| 449 | " | " | " | " | " | " | $-OC_2H_5$ |
| 450 | " | " | " | $CH_2$ | $CH_2$ | " | $-OCH_3$ |
| 451 | " | " | " | " | " | " | $-OC_2H_5$ |
| 452 | " | " | " | — | $CH_2$ | " | $-OCH_3$ |
| 453 | " | " | " | " | " | " | $-OC_2H_5$ |

TABLE 5

$$\begin{array}{c} R^1 \\ R^2-Si-A-\underset{X-N}{\bigcirc}-B-CO-Z \\ R^3 \end{array} \quad (5)$$

| Example | R¹ | R² | R³ | A | B | X | Z | mp/n$_D^{20}$ |
|---|---|---|---|---|---|---|---|---|
| 454 | CH₃ | CH₃ | CH₃ | — | — | O | —OCH₃ | |
| 455 | " | " | " | " | " | " | —OC₂H₅ | |
| 456 | " | " | " | CH₂ | — | O | —OCH₃ | |
| 457 | " | " | " | " | " | " | —OC₂H₅ | |
| 458 | " | " | " | " | CH₂ | " | —OCH₃ | |
| 459 | " | " | " | " | " | " | —OC₂H₅ | |
| 460 | " | " | " | — | CH₂ | " | —OCH₃ | |
| 461 | " | " | " | — | CH₂ | " | —OC₂H₅ | |
| 462 | " | " | " | — | — | S | —OCH₃ | |
| 463 | " | " | " | " | " | " | —OC₂H₅ | |
| 464 | " | " | " | CH₂ | — | " | —OCH₃ | |
| 465 | " | " | " | " | " | " | —OC₂H₅ | |
| 466 | " | " | " | CH₂ | CH₂ | " | —OCH₃ | |
| 467 | " | " | " | " | " | " | —OC₂H₅ | |
| 468 | " | " | " | — | CH₂ | " | —OCH₃ | |
| 469 | " | " | " | " | " | " | —OC₂H₅ | |
| 479 | " | " | " | CH₂ | CH₂ | O | —CH₂C≡CH | |
| 471 | " | " | " | — | — | " | —CH₂C≡CH | |
| 472 | " | " | " | CH₂ | — | " | —CH₂C≡CH | |
| 473 | " | " | " | — | CH₂ | " | —CH₂C≡CH | |
| 474 | " | " | " | — | — | S | —CH₂C≡CH | |
| 475 | " | " | " | — | — | S | —CH₂CH=CH₂ | |
| 476 | " | " | " | — | — | O | —CH₂CH=CH₂ | |
| 477 | " | " | " | — | — | O | —(CH₂)₃CH₃ | |
| 478 | " | " | " | — | — | S | —(CH₂)₃CH₃ | |
| 479 | " | " | " | — | — | S | OH | |
| 480 | " | " | " | — | — | O | OH | |
| 481 | CH₃ | CH₃ | CH₃ | CH₂ | CH₂ | O | OH | |
| 482 | " | " | " | CH₂ | — | O | OH | |
| 483 | " | " | " | — | CH₂ | O | OH | |
| 484 | " | " | " | — | CH₂ | S | OH | |
| 485 | " | " | " | CH₂ | — | S | OH | |

TABLE 6

$$\begin{array}{c} R^1 \\ R^2-Si-A-\underset{N\ X}{\bigcirc}-B-CO-Z \\ R^3 \end{array} \quad (6)$$

| Example | R¹ | R² | R³ | A | B | X | Z | mp/n$_D^{20}$ |
|---|---|---|---|---|---|---|---|---|
| 486 | " | " | " | — | — | O | OH | |
| 487 | " | " | " | — | — | S | OH | |
| 488 | " | " | " | CH₂ | CH₂ | O | OH | |
| 489 | " | " | " | CH₂ | — | O | OH | |
| 490 | CH₃ | CH₃ | CH₃ | — | — | O | —OCH₃ | |
| 491 | " | " | " | " | " | " | —OC₂H₅ | |
| 492 | " | " | " | CH₂ | — | O | —OCH₃ | |
| 493 | " | " | " | " | " | " | —OC₂H₅ | |
| 494 | " | " | " | " | CH₂ | " | —OCH₃ | |
| 495 | " | " | " | " | " | " | —OC₂H₅ | |
| 496 | " | " | " | — | CH₂ | " | —OCH₃ | |
| 497 | " | " | " | — | CH₂ | " | —OC₂H₅ | |
| 498 | " | " | " | — | — | S | —OCH₃ | |
| 499 | " | " | " | " | " | " | —OC₂H₅ | |
| 500 | " | " | " | CH₂ | — | " | —OCH₃ | |
| 501 | " | " | " | " | " | " | —OC₂H₅ | |
| 502 | " | " | " | CH₂ | CH₂ | " | —OCH₃ | |
| 503 | " | " | " | " | " | " | —OC₂H₅ | |
| 504 | " | " | " | — | CH₂ | " | —OCH₃ | |
| 505 | " | " | " | " | " | " | —OC₂H₅ | |
| 506 | " | " | " | CH₂ | CH₂ | O | —CH₂C≡CH | |
| 507 | " | " | " | — | — | " | —CH₂C≡CH | |
| 508 | " | " | " | CH₂ | — | " | —CH₂C≡CH | |
| 509 | " | " | " | — | CH₂ | " | —CH₂C≡CH | |
| 510 | " | " | " | — | — | S | —CH₂C≡CH | |
| 511 | " | " | " | — | — | S | —CH₂CH=CH₂ | |
| 512 | " | " | " | — | — | O | —CH₂CH=CH₂ | |
| 513 | " | " | " | — | — | O | —(CH₂)₃CH₃ | |
| 514 | " | " | " | — | — | S | —(CH₂)₃CH₃ | |

C. Biological Examples

Wheat and barley were grown in plastic pots in a greenhouse until they had reached the 3-4 leaf stage, and then treated with the compounds according to the invention and herbicides, using the post-emergence method. For this purpose, the herbicides and the compounds of the formula (I) were applied in the form of aqueous suspensions or emulsions, at an application rate of water of 800 l/ha (converted). 3-4 weeks after the treatment, the plants were visually scored for any type of damage caused by the herbicides applied, the extent of sustained growth inhibition being particularly taken into account. For the assessment, percentages in comparison with untreated controls were used.

The results from Table 7 show that the compounds according to the invention are capable of effectively reducing severe herbicide damage on crop plants.

Even when far too high doses of the herbicides are applied, severe damage which occurs in the crop plants is markedly reduced, and lesser damage is eliminated completely. Mixtures of herbicides and compounds according to the invention are therefore highly suitable for selectively controlling weeds in cereal crops.

TABLE 7

| Safener action of the compounds according to the invention | | | |
|---|---|---|---|
| Herbicide (H) + safener No. | Dosage rate in kg of a.i./ha | Damage to crop plant (%) | |
| | | TRAE | HOVU |
| H | 2.0 | 80 | — |
| | 0.2 | — | 85-90 |
| H + 2 | 2.0 + 1.25 | 20 | — |
| H + 3 | 0.2 + 1.25 | — | 30 |
| H + 4 | 2.0 + 1.25 | 25 | — |
| H + 261 | 0.2 + 1.25 | — | 35 |

Abbreviations:
TRAE = *Triticum aestivum* (wheat)
HOVU = *Hordeum vulgare* (barley)
a.i. = active ingredient (i.e. based on pure active substance)
H = ethyl 2-(4-(6-chlorobenzoxazol-2-yloxy)phenoxypropionate (fenoxaprop-ethyl)
Safener No. = No. of the Preparation Example of Tables 1-6

We claim:

1. A compound of the formula (I) and salts thereof

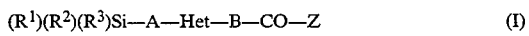

in which
Het is a divalent heterocyclic radical from the group comprising the isothiazolines, isothiazoles or isoxazoles, and isoxazolines of the formulae (Ia) to (Id),

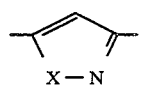 (Ia)

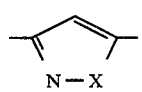 (Ib)

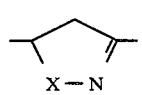 (Ic)

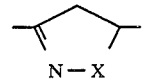 (Id)

in which
X is an oxygen or sulfur atom,
A and B independently of one another in each case are a single bond or $C_1$-$C_4$-alkylene which is unsubstituted or monosubstituted or polysubstituted by $C_1$-$C_4$-alkyl,
$R^1$, $R^2$ and $R^3$ independently of one another are alkyl, alkenyl, alkynyl or cycloalkyl, it being possible for the four last-mentioned radicals to be unsubstituted or mono- or polysubstituted by radicals from the group comprising alkoxy, alkylthio, mono- or dialkylamino, alkoxycarbonyl, alkylcarbonyloxy, cyano and halogen, furthermore phenylalkyl or phenyl which in each case are unsubstituted or mono- or polysubstituted in the phenyl radical by radicals from the group comprising alkyl, alkoxy, alkylthio, mono- and dialkylamino, alkoxycarbonyl, cyano and halogen,
Z is hydroxyl or alkoxy, alkenyloxy, alkynyloxy, alkylthio, cycloalkoxy, phenoxy or benzyloxy, the 7 last-mentioned radicals being unsubstituted or mono- or polysubstituted by radicals from the group comprising alkoxy, alkylthio, mono- and dialkylamino, phenyl, substituted phenyl, cyano, halogenoalkyl, halogenoalkoxy and halogen, furthermore trialkylsilylmethoxy, a radical of the formula (Ie) or (If)

 (Ie)

or

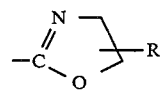 (If)

where R is hydrogen or alkyl, $Z^1$ radicals independently of one another are halogen, haloalkyl, haloalkoxy, alkyl, alkoxy or alkylthio and n is an integer from 0 to 5, or
Z is furthermore amino, mono- or dialkylamino, cycloalkylamino, hydrazino, alkyl- or dialkylhydrazino, pyridino, morpholino, dimethylmorpholino, a radical of the formula (Ig),

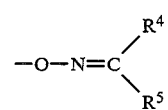 (Ig)

where $R^4$ and $R^5$ independently of one another are alkyl radicals or $R^4$ and $R^5$ together with the carbon atom linking them forte a cycloalkyl radical, furthermore a radical of the formula (Ih),
where $R^6$ and $R^7$ independently of one another are hydrogen or a saturated or unsaturated acyclic hydrocarbon radical.

2. A compound and salts thereof as claimed in claim 1, in which
   Z is hydroxyl, $C_1$-$C_6$-alkoxy, $C_2$-$C_6$-alkenyloxy, $C_2$-$C_6$-alkynyloxy, $C_1$-$C_6$-alkylthio, $C_3$-$C_6$-cycloalkoxy, phenoxy or benzyloxy, the 7 last-mentioned radicals being unsubstituted or mono- or polysubstituted by radicals from the group comprising $C_1$-$C_4$-alkoxy, mono- or di-($C_1$-$C_4$-alkyl)amino, $C_1$-$C_4$-alkylthio, $C_1$-$C_4$-haloalkyl, $C_1$-$C_4$-haloalkoxy, cyano and halogen, or
   Z is furthermore tri($C_1$-$C_4$-alkyl)silylmethoxy, furthermore a radical of the formula (Ie) or (If) mentioned, in which R in each case is hydrogen or ($C_1$-$C_4$)-alkyl, $Z^1$ is halogen and n is 0, 1, 2, 3, 4 or 5, or
   Z is furthermore amino, mono- or di-($C_1$-$C_4$-alkyl)-amino, $C_5$-$C_6$-cycloalkylamino, hydrazino, piperidino, morpholino or 2,6-dimethylmorpholino, a radical of the formula (Ig) mentioned where $R^4$ and $R^5$ independently of one another are $C_1$-$C_4$-alkyl or $R^1$ and $R^2$ together with the carbon atom linking them form a 5-, 6- or 7-membered cycloalkyl radical, or
   Z is a radical of the formula (Ih) mentioned where $R^6$ and $R^7$ independently of one another are hydrogen or $C_1$-$C_6$-alkyl, $C_2$-$C_6$-alkyl or $C_2$-$C_6$-alkynyl.

3. A compound and salts thereof as claimed in claim 2, in which
   $R^1$, $R^2$ and $R^3$ independently of one another are $C_1$-$C_{18}$-alkyl, $C_2$-$C_{18}$-alkenyl, $C_2$-$C_8$-alkynyl or $C_3$-$C_8$-cycloalkyl, the 4 last-mentioned radicals being unsubstituted or mono- or polysubstituted by radicals from the group comprising $C_1$-$C_4$-alkyl, $C_1$-$C_4$-alkylthio, mono- or di-($C_1$-$C_4$-alkyl)amino, ($C_1$-$C_4$-alkoxy)carbonyl, ($C_1$-$C_4$-alkyl)carbonyloxy, cyano and halogen, furthermore phenyl-($C_1$-$C_4$-alkyl) or phenyl, the 2 last-mentioned radicals being unsubstituted or mono- or polysubstituted by radicals from the group comprising $C_1$-$C_4$-alkyl, $C_1$-$C_4$-alkoxy, $C_1$-$C_4$-alkylthio, mono- and di-($C_1$-$C_4$-alkyl)amino, cyano and halogen.

4. A compound and salts thereof as claimed in claim 3, in which
   Z is hydroxyl, $C_1$-$C_4$-alkoxy, $C_2$-$C_4$-alkynyloxy, $C_2$-$C_4$-alkynyloxy, $C_1$-$C_4$-alkylthio, phenoxy or benzyloxy, the 6 last-mentioned radicals being unsubstituted or mono- or polysubstituted by radicals from the group comprising $C_1$-$C_4$-alkyl, $C_1$-$C_4$-alkoxy, $C_1$-$C_4$-alkylthio, mono- or di-($C_1$-$C_4$-alkyl)amino, cyano and halogen, furthermore tri-($C_1$-$C_2$-alkyl)silylmethoxy, a radical of the formula (Ie) or (If) mentioned where R is hydrogen or $C_1$-$C_4$-alkyl, $Z^1$ is halogen and n is 0-5, furthermore mono- and di-($C_1$-$C_4$-alkyl)amino, $C_5$-$C_6$-cycloalkylamino, a radical of the formula (Ih) mentioned where $R^6$ is $C_1$-$C_4$-alkyl, $C_2$-$C_4$-alkenyl or $C_2$-$C_6$-alkynyl and $R^7$ is hydrogen or methyl.

5. A compound and salts thereof as claimed in one of claims 1 to 4, in which
   A is a direct bond or $C_1$-$C_2$-alkylene, preferably a direct bond or $CH_2$, and
   B is a direct bond or $C_1$-$C_2$-alkylene.

6. A plant-protecting or plant-growth-regulating agent which contains a compound of the formula (I) or salts thereof, as claimed in claim 1, and inert additives or formulation auxiliaries.

7. A selective herbicidal agent, which contains one or more herbicides in combination with a compound of the formula (I) or salts thereof, as defined in claim 1.

8. An agent as claimed in claim 7, which contains, as herbicides, one or more active substances from the group comprising carbamates, thiocarbonates, haloacetanilides, substituted phenoxy-, naphthoxy-, phenoxyphenoxy-, benzyloxyphenoxy- and heteroaryloxyphenoxy-carboxylic acid derivatives and cyclohexanedione derivatives.

9. A method of selectively controlling undesired plants in crops of useful plants, which comprises applying, to the plants, seeds of plants or the area under cultivation, a herbicide in combination with compounds of the formula (I) or salts thereof, as defined in claim 1.

10. A method of protecting useful plants against phytotoxic side effects of herbicides, which comprises applying, to the plants, seeds of plants or the area under cultivation, herbicides in combination with compounds of the formula (I) or salts thereof, as defined in claim 1.

11. A compound and salts thereof as claimed in claim 5, wherein A is a direct bond or $CH_2$, and B is a direct bond or $CH_2$.

12. A plant-protecting or plant-growth-regulating agent which contains a compound of the formula (I) or salts thereof, as claimed in claim 11, and inert additives or formulation auxiliaries.

13. A selective herbicidal agent, which contains one or more herbicides selected from the group consisting of carbamates, thiocarbamates, haloacetanilides, substituted phenoxy-, naphthoxy-, phenoxyphenoxy-, benzyloxyphenoxy- and heteroaryloxyphenoxy-carboxylic acid derivatives and cyclohexanedione derivatives, in combination with the compound of formula (I) as defined in claim 11.

14. A selective herbicidal agent as claimed in claim 13, wherein the herbicide is selected from the group consisting of heteroaryloxyphenoxy-carboxylic acid derivatives.

* * * * *